United States Patent [19]
Halbich

[11] Patent Number: 5,716,345
[45] Date of Patent: Feb. 10, 1998

[54] HYPODERMIC SYRINGE FILLING APPARATUSES AND HYPODERMIC SYRINGE GRASPING APPARATUSES

[76] Inventor: Frank Halbich, 4595 W. Selway Ave., Post Falls, Id. 83854

[21] Appl. No.: 779,715

[22] Filed: Jan. 7, 1997

Related U.S. Application Data

[63] Continuation-in-part of Ser. No. 606,735, Feb. 27, 1996, Pat. No. 5,620,422.

[51] Int. Cl.$^6$ .................................................. A61M 5/00
[52] U.S. Cl. .................................................. 604/207; 141/27
[58] Field of Search ........................... 604/187, 207–211, 604/218, 192, 263; 141/27, 28, 94, 95

[56] References Cited

U.S. PATENT DOCUMENTS

| | | | |
|---|---|---|---|
| 3,833,030 | 9/1974 | Waldbauer, Jr. et al. | 604/208 |
| 3,964,139 | 6/1976 | Kleinmann et al. | 604/187 X |
| 3,965,945 | 6/1976 | Ross | 604/211 |
| 4,022,207 | 5/1977 | Citrin | 604/209 |
| 4,252,159 | 2/1981 | Maki | 141/27 |
| 4,434,820 | 3/1984 | Glass | 141/27 X |
| 4,518,387 | 5/1985 | Murphy et al. | 604/187 |
| 4,846,803 | 7/1989 | Emerson | 604/192 X |
| 5,468,233 | 11/1995 | Schraga | 604/207 |

*Primary Examiner*—John D. Yasko
*Attorney, Agent, or Firm*—Wells, St. John, Roberts, Gregory & Matkin, P.S.

[57] ABSTRACT

Hypodermic syringe filling apparatuses and grasping apparatuses. The invention includes a hypodermic syringe grasping apparatus comprising: a) a pair of syringe support members configured for pushing inwardly on a syringe held between them; at least one of the pivotal syringe support members comprising: b) a syringe grasping portion comprising a first curved portion and a second curved portion; the first and second curved portions comprising a first curvature and a second curvature, respectively; and c) the pair of pivotal syringe support members together comprising an upwardly open cradle sized and shaped to externally engage a cylindrical syringe barrel portion of a hypodermic syringe. The invention also includes a hypodermic syringe filling apparatus enabling filling of a hypodermic syringe with a prescribed quantity of fluid, the filling apparatus comprising: a) a pair of pivotal syringe support members configured for pushing inwardly on a syringe held between them; the respective pivotal syringe support members comprising: b) pinch arm portions; c) syringe grasping cupped portions adjacent the pinch arm portions; and d) wherein the pair of pivotal syringe support members comprise lengths and widths; the syringe filling apparatus further comprising a space between the pivotal syringe support members spanning the lengths and widths of the pivotal syringe support members.

36 Claims, 13 Drawing Sheets

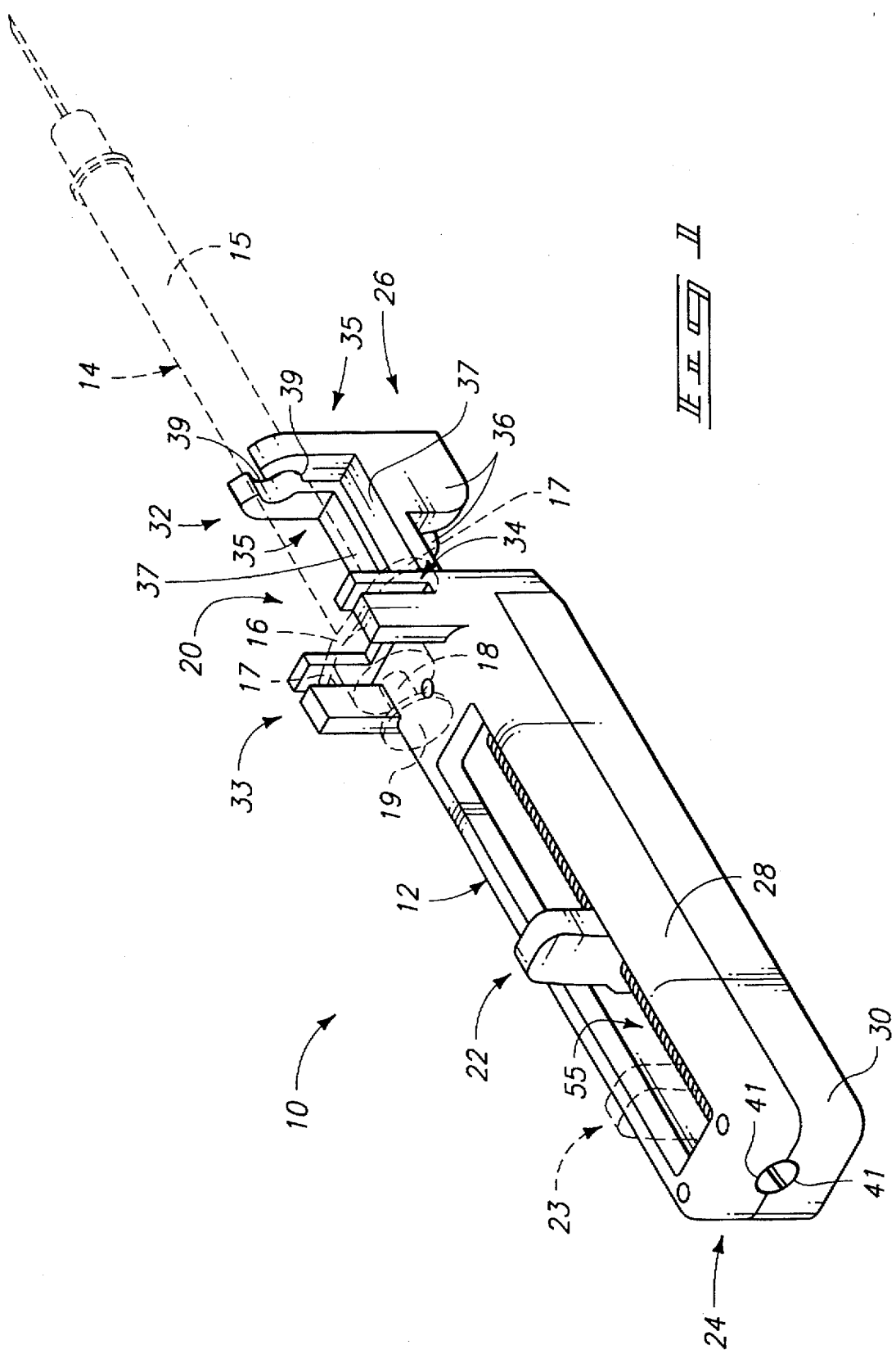

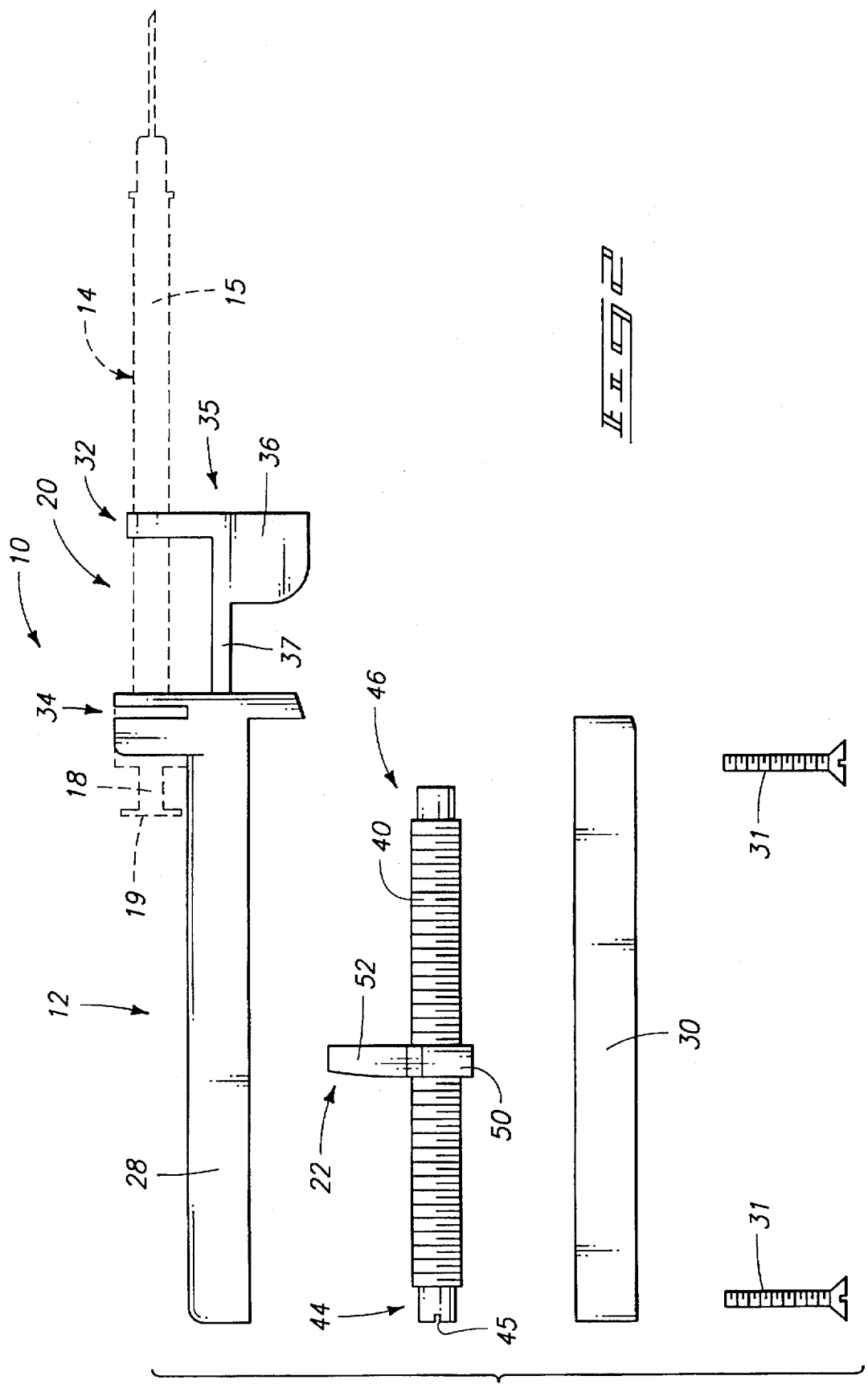

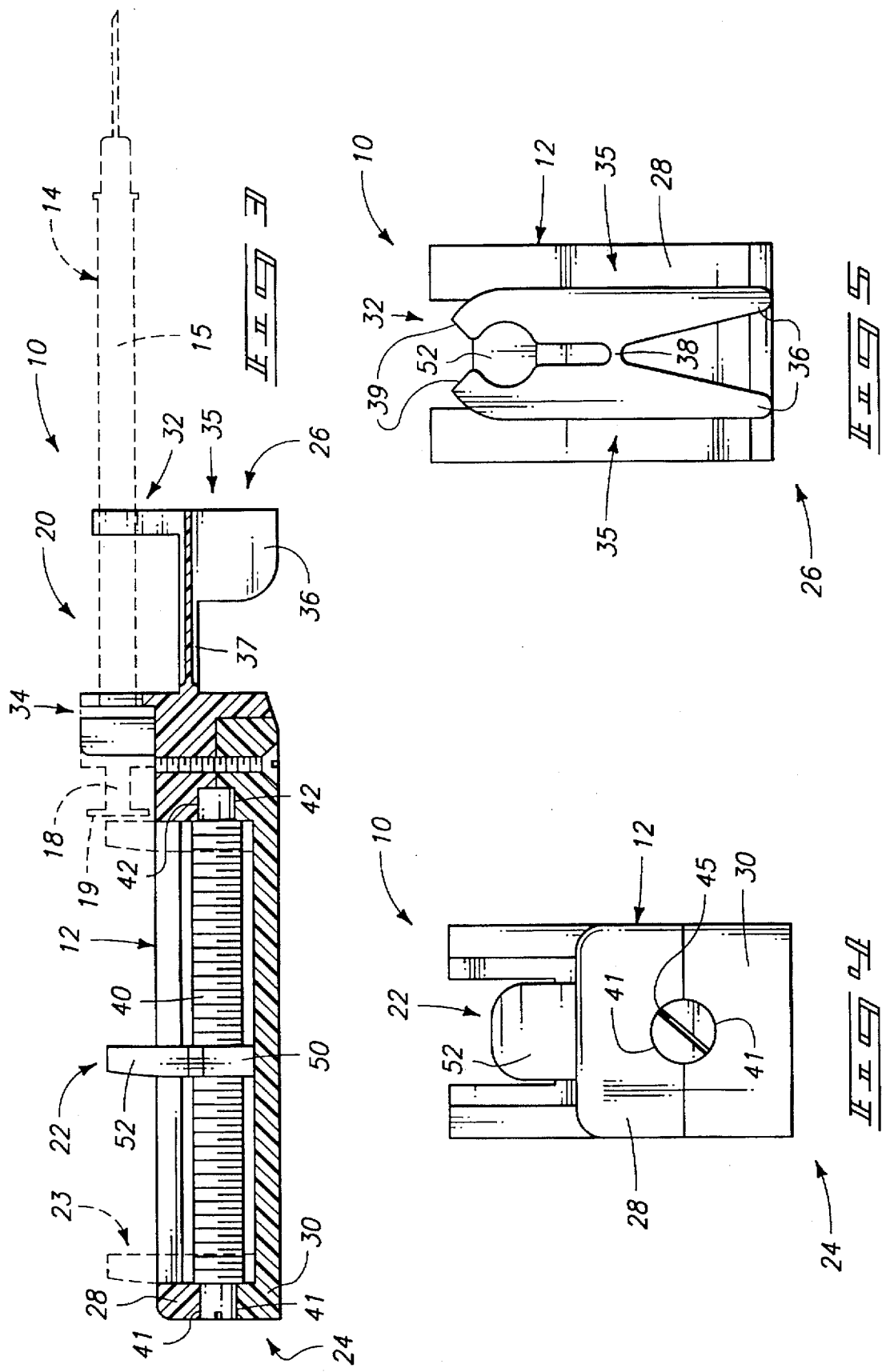

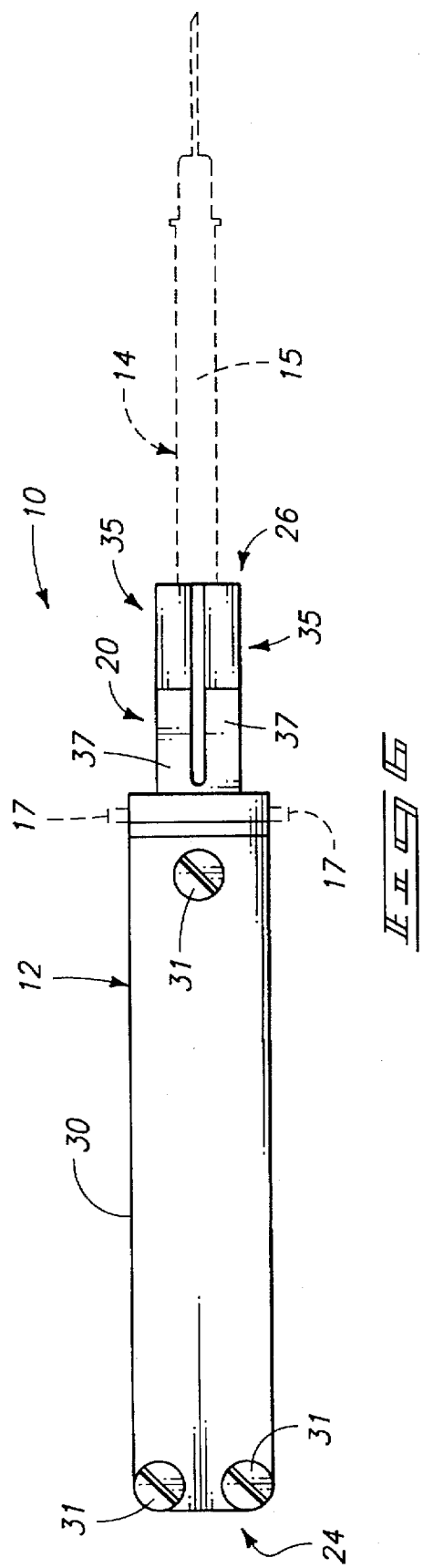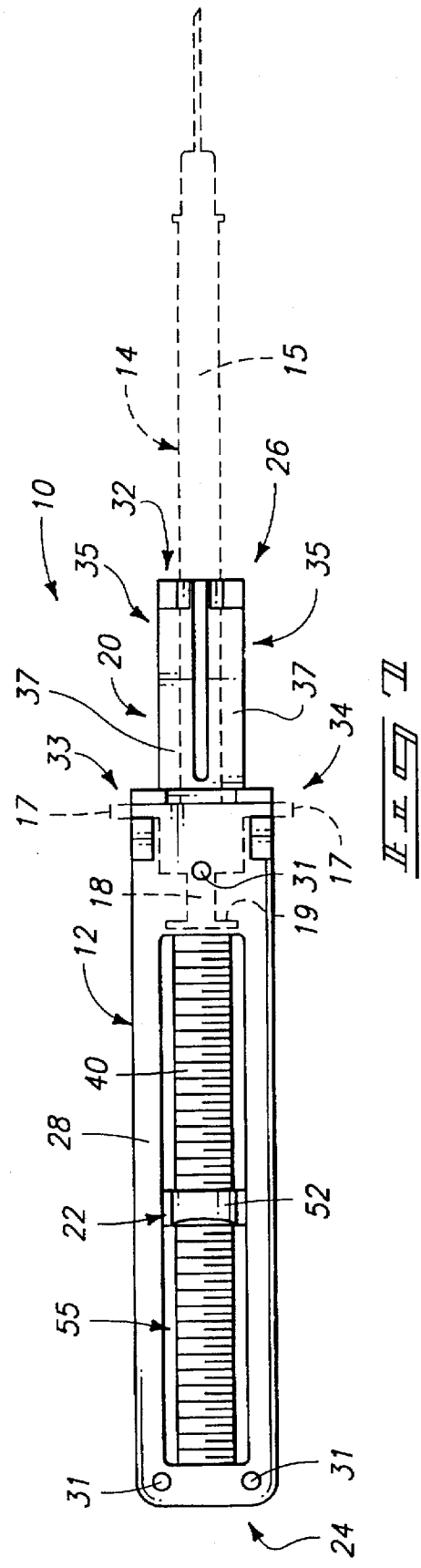

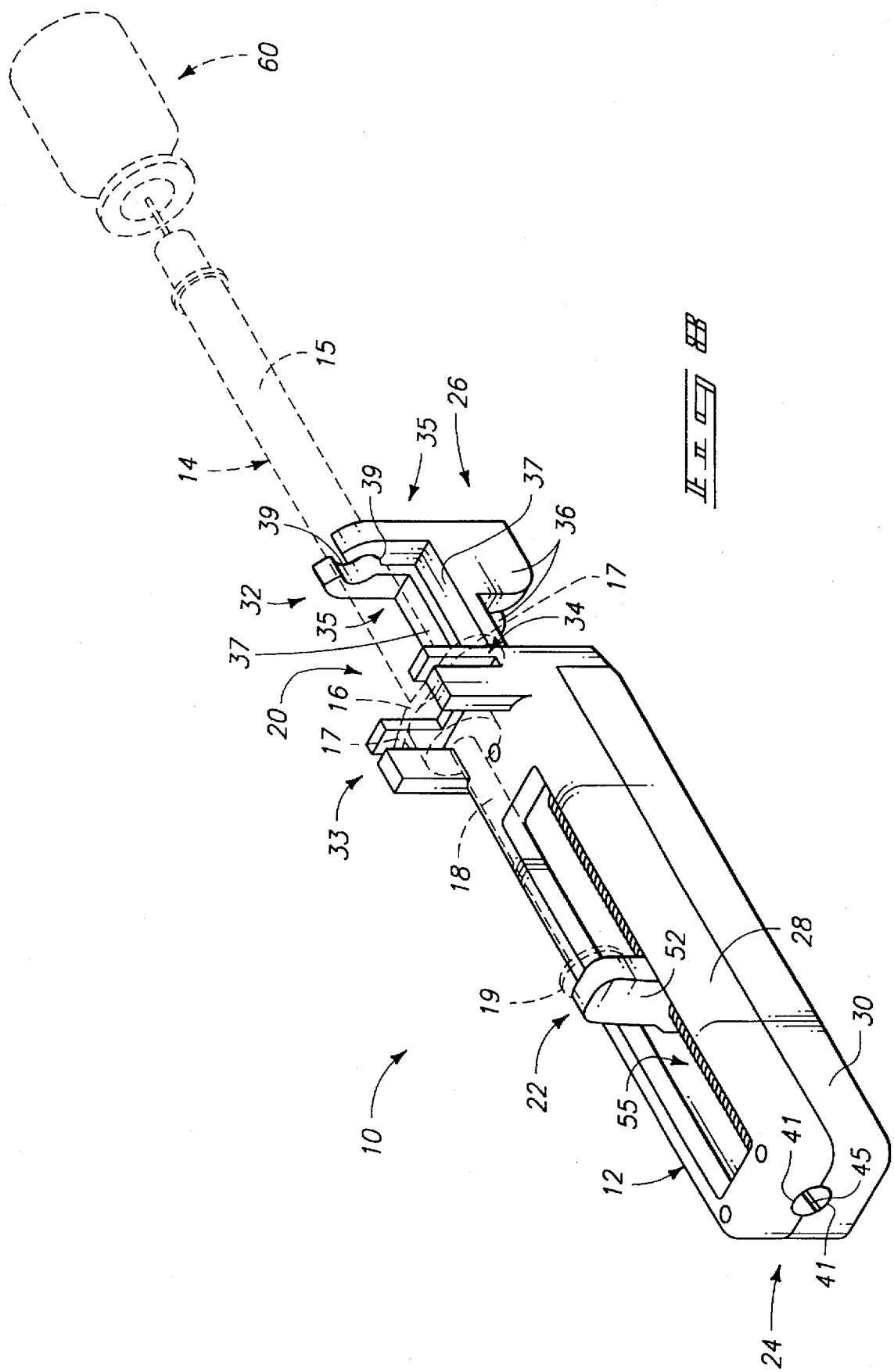

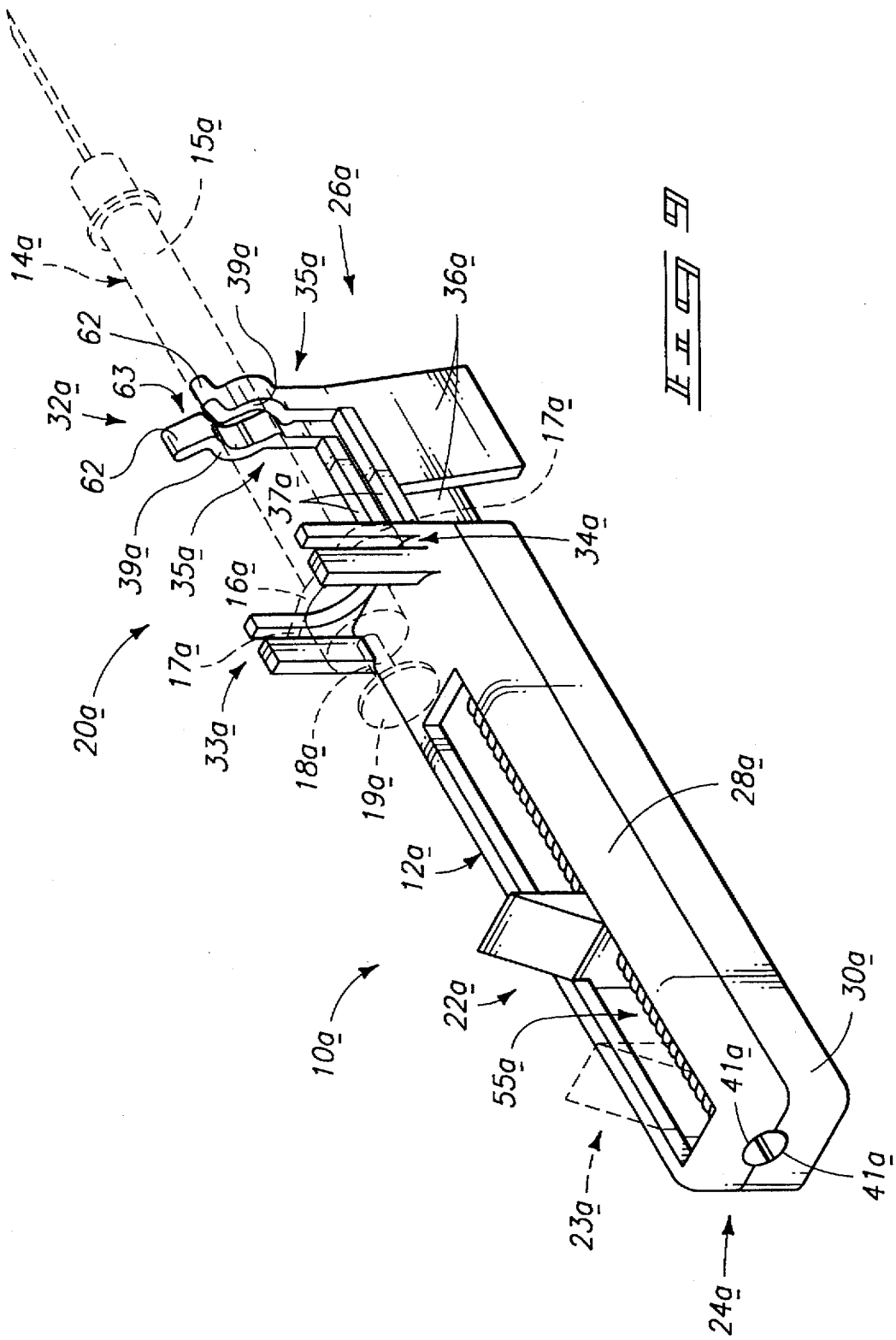

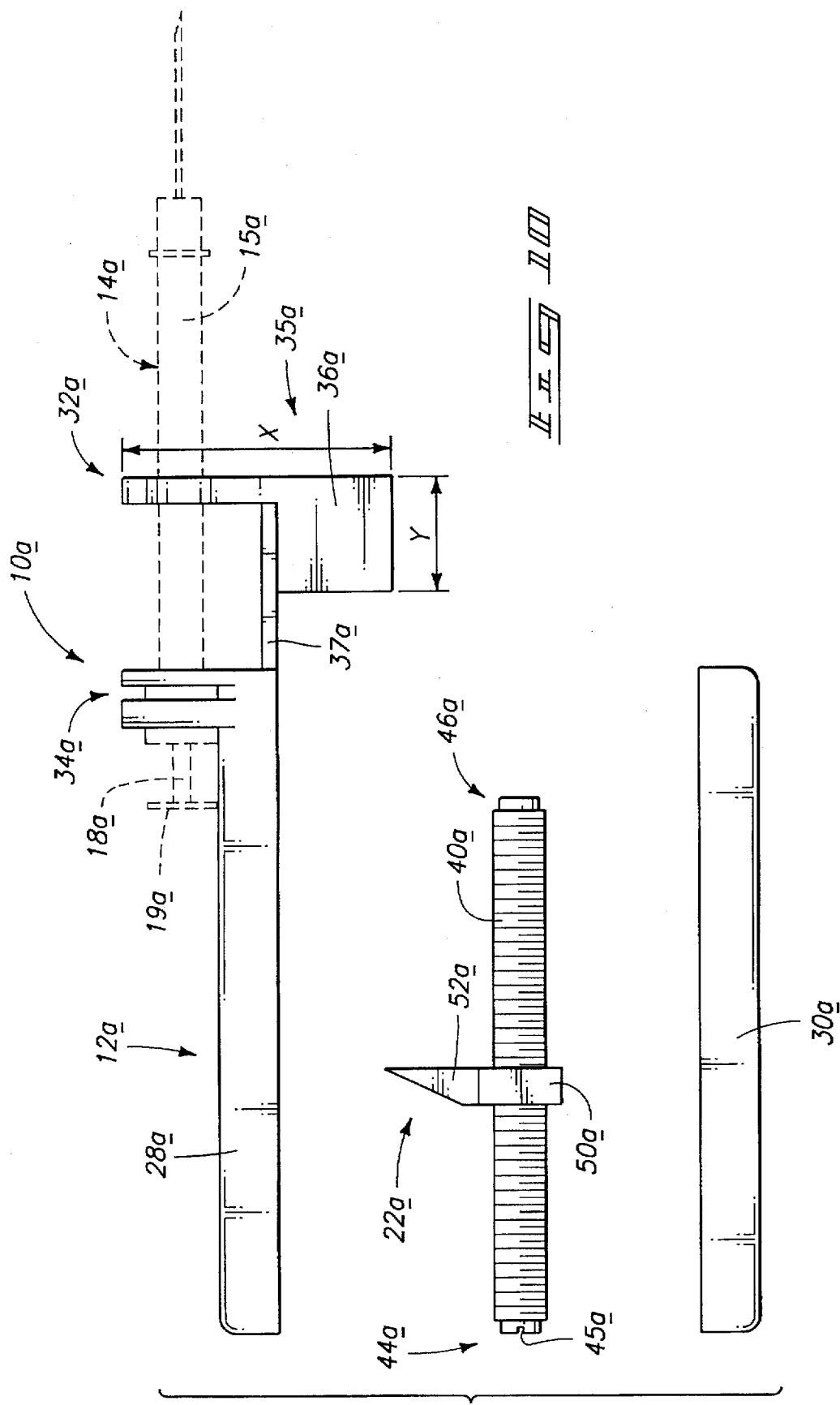

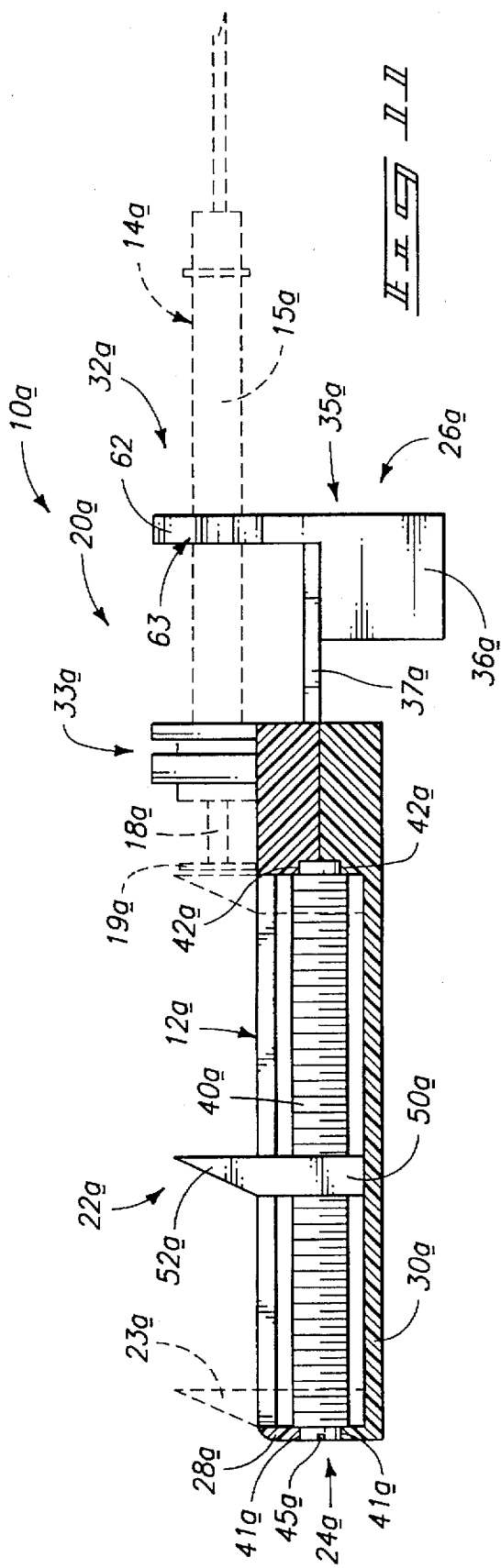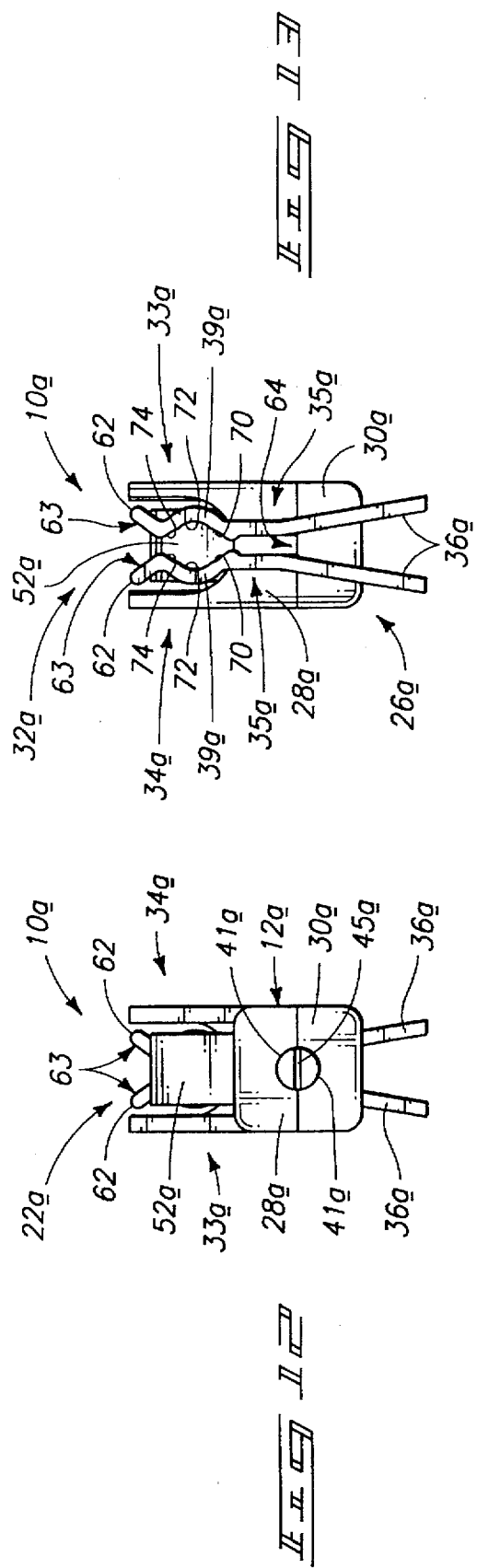

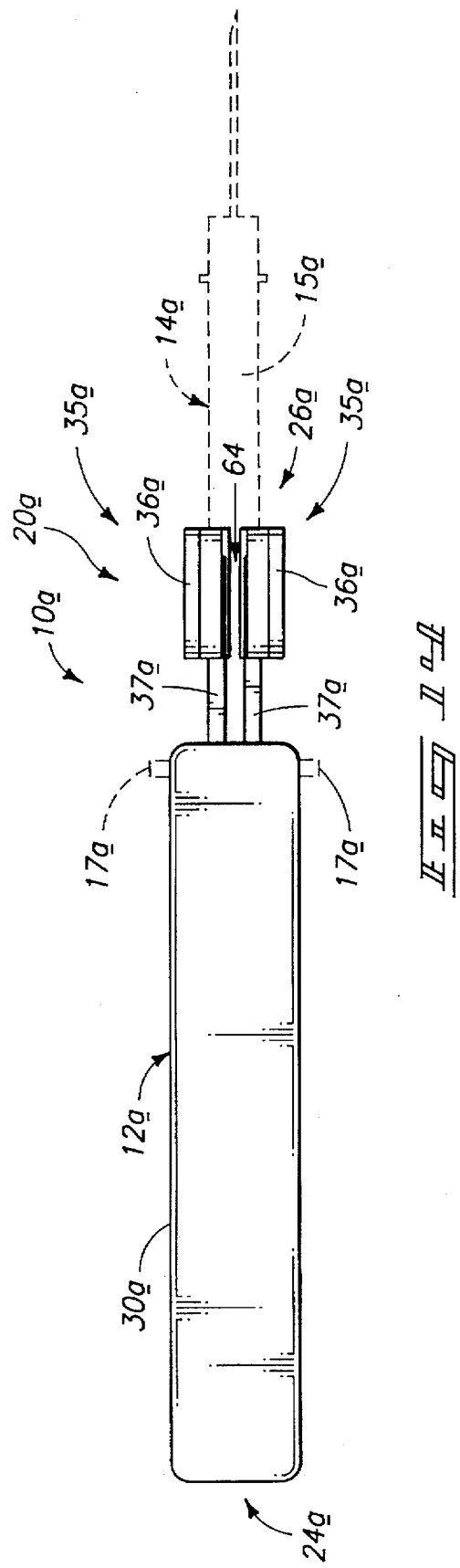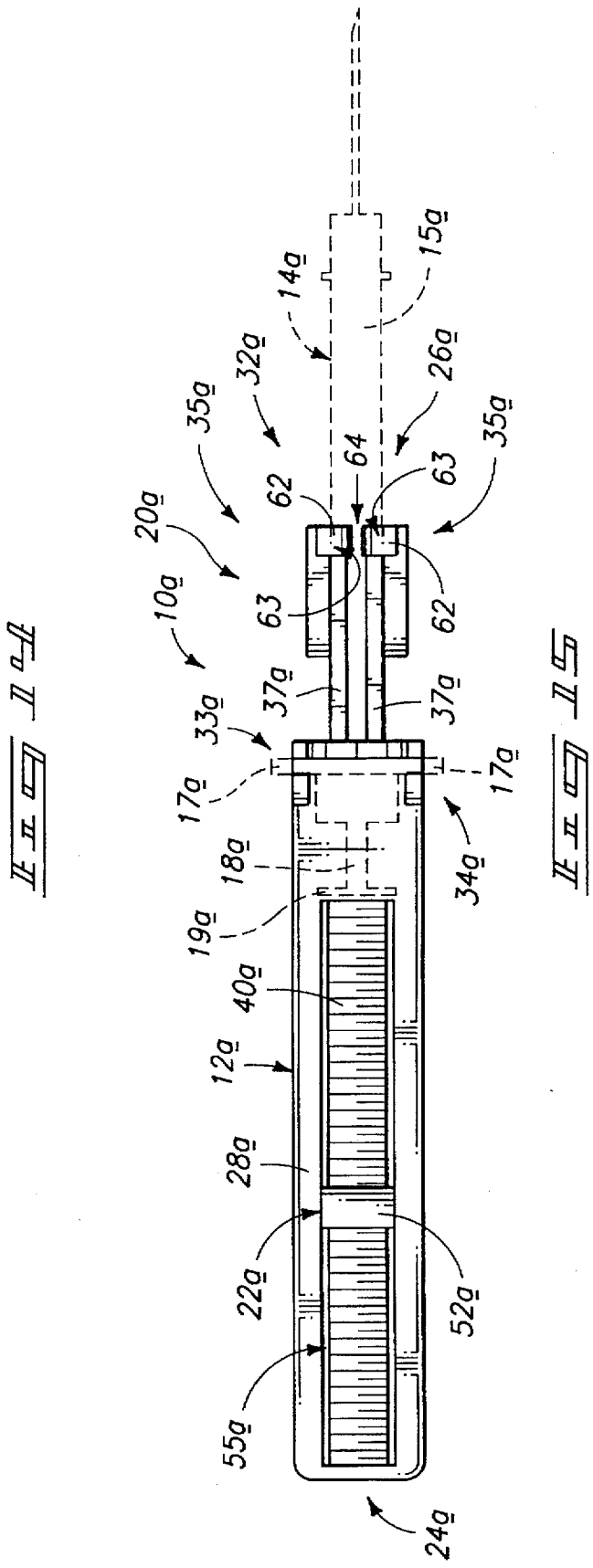

HYPODERMIC SYRINGE FILLING APPARATUSES AND HYPODERMIC SYRINGE GRASPING APPARATUSES

RELATED PATENT DATA

This patent resulted from a continuation-in-part application of U.S. patent application Ser. No. 08/606,735, filed on Feb. 27, 1996, now U.S. Pat. No. 5,620,422 entitled "A Hypodermic Syringe Filling Apparatus" listing the inventor as Frank Halbich.

TECHNICAL FIELD

This invention relates to hypodermic syringe filling devices and hypodermic syringe grasping devices.

BACKGROUND OF THE INVENTION

Many patients under the direction of a physician provide themselves with periodic doses of medication by hypodermic injection. Probably the most common instance of such is the insulin injections that diabetics must provide themselves with on a daily basis.

One thing key to providing such injections is to insure that the correct dose is administered with each injection. To fill the syringe, the patient typically inserts the needle of the syringe into a vial containing the desired medication. The syringe plunger is then withdrawn and stopped at a location relative to gradation markings on the outside of the syringe to assure that a proper quantity of medication liquid is withdrawn into the syringe barrel. Such a procedure can however be difficult or impossible for the blind or other visually impaired people.

One technique to overcome such drawback would be for the pharmacist to provide the patient with pre-filled syringes having the desired quantity of medication provided therein. This would undesirably however require that the manufacturer provide various syringes filled with various medications at selected dosages, or require the pharmacist to fill a series of syringes for the patients with the correct medication and dosages. Neither of these alternatives is very desirable. In the first, considerable expense would be associated with the manufacturer providing a plurality of syringes with various medication at various dosages. Having a pharmacist provide the filled syringes would breach the sterile field of the syringes, subjecting the patient to greater risk of infection.

Accordingly, a need remains to assist the visually impaired and other people to, in a more automated way, provide filling of a syringe with the desired medication to a predetermined dosage.

BRIEF DESCRIPTION OF THE DRAWINGS

Preferred embodiments of the invention are described below with reference to the following accompanying drawings.

FIG. 1 is a perspective view of a hypodermic syringe filling apparatus in accordance with a first embodiment of the present invention.

FIG. 2 is an exploded view of the FIG. 1 syringe filling apparatus.

FIG. 3 is a longitudinal sectional view of the FIG. 1 syringe filling apparatus.

FIG. 4 is a rear end view of the FIG. 1 syringe filling apparatus.

FIG. 5 is a front end view of the FIG. 1 syringe filling apparatus.

FIG. 6 is a bottom longitudinal view of the FIG. 1 syringe filling apparatus.

FIG. 7 is a top longitudinal view of the FIG. 1 syringe filling apparatus.

FIG. 8 is another perspective view of the FIG. 1 syringe filling apparatus shown with a plunger of a hypodermic syringe received by the apparatus in a fully extended position relative to the illustrated adjustment of the apparatus.

FIG. 9 is a perspective view of a hypodermic syringe filling apparatus in accordance with a second embodiment of the invention.

FIG. 10 is an exploded view of the FIG. 9 syringe filling apparatus.

FIG. 11 is a longitudinal sectional view of the FIG. 9 syringe filling apparatus.

FIG. 12 is a rear end view of the FIG. 9 syringe filling apparatus.

FIG. 13 is a front end view of the FIG. 9 syringe filling apparatus.

FIG. 14 is a bottom longitudinal view of the FIG. 9 syringe filling apparatus.

FIG. 15 is a top longitudinal view of the FIG. 9 syringe filling apparatus.

DETAILED DESCRIPTION OF THE PREFERRED EMBODIMENTS

Figure 16:
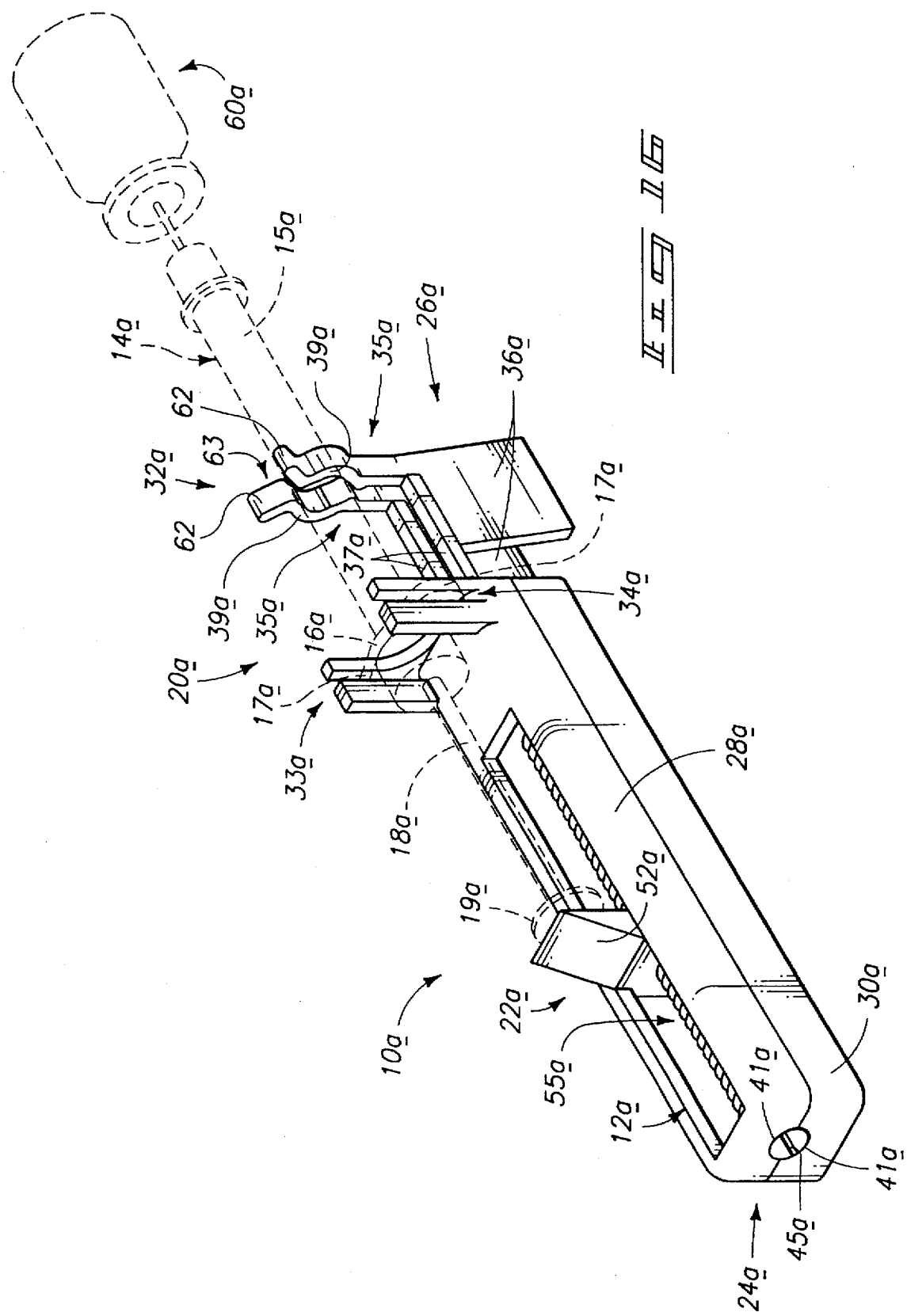
FIG. 16 is another perspective view of the FIG. 9 syringe filling apparatus shown with a plunger of a hypodermic syringe received by the apparatus in a fully extended position relative to the illustrated adjustment of the apparatus.

This disclosure of the invention is submitted in furtherance of the constitutional purposes of the U.S. Patent Laws "to promote the progress of science and useful arts" (Article 1, Section 8).

In one aspect, the invention includes a hypodermic syringe filling apparatus enabling filling of a hypodermic syringe with a prescribed quantity of fluid, the filling apparatus comprising:

a pair of pivotal syringe support members configured for pushing inwardly on a syringe held between them; the respective pivotal syringe support members comprising:

pinch arm portions;

syringe grasping cupped portions adjacent the pinch arm portions, the syringe grasping cupped portions comprising first, second and third radial portions; the second radial portion being positionally between the first and the third radial portions; the first, second and third radial portions comprising segments of first, second, and third circles, respectively, the second circle comprising a smaller radius than the first and third circles;

syringe slide portions adjacent the syringe grasping cupped portions; and the pair of pivotal syringe support members together comprising an upwardly open cradle sized and shaped to externally engage a cylindrical syringe barrel portion of a hypodermic syringe.

In another aspect, the invention includes a hypodermic syringe filling apparatus enabling filling of a hypodermic syringe with a prescribed quantity of fluid, the filling apparatus comprising:

a pair of pivotal syringe support members configured for pushing inwardly on a syringe held between them; the respective pivotal syringe support members comprising:

pinch arm portions;

syringe grasping cupped portions adjacent the pinch arm portions; and wherein the pair of pivotal syringe support members comprise lengths and widths; the syringe filling apparatus further comprising a space between the pivotal syringe support members spanning the lengths and widths of the pivotal syringe support members.

In yet another aspect, the invention includes a hypodermic syringe grasping apparatus comprising:

a pair of syringe support members configured for pushing inwardly on a syringe held between them; at least one of the pivotal syringe support members comprising:

a syringe grasping portion comprising a first curved portion and a second curved portion; the first and second curved portions comprising a first curvature and a second curvature, respectively; and the pair of pivotal syringe support members together comprising an upwardly open cradle sized and shaped to externally engage a cylindrical syringe barrel portion of a hypodermic syringe.

Referring initially to FIGS. 1–8, a first embodiment of a hypodermic syringe filling apparatus enabling filling of a hypodermic syringe with a prescribed quantity of fluid is indicated generally with reference numeral 10. Such comprises a longitudinally elongated body 12 configured for retaining a hypodermic syringe 14. For purposes of the continuing discussion, the illustrated example syringe 14 comprises a cylindrical barrel portion 15, a syringe finger flange 16 having opposing flange ears 17, a plunger 18 slidably received within barrel 15, and a plunger head/end 19.

A syringe supporting framework 20 is provided relative to body 12 and is sized to externally engage and retain hypodermic syringe 14. A plunger stop 22 is associated with body 12 and positioned to engage and stop extension of plunger 18 of syringe 14 received by supporting framework 20. Plunger stop 22 is mounted for movement relative to supporting framework 20 to a plurality of fixed locations to enable degree of extension of plunger 18 to be selectively varied.

Body 12 comprises a pair of juxtaposed pieces in the form of an upper portion 28 and a lower portion 30 which are retained together by a series of three screws 31. The preferred material of construction for screws 31 is stainless steel, with the various other illustrated components preferably comprising any suitable plastic. Other mechanisms for interconnecting body halves 28 and 30, instead of, or in addition to, the screws 31 may be utilized. For instance, the upper portion 28 and the lower portion 30 may be interconnected by a weld, such as would be formed by a sonic welding process.

Elongated body 12 has opposing longitudinal ends 24 and 26. Syringe supporting framework 20 is provided at or adjacent longitudinal end 26, and in the shown preferred embodiment is formed at a fore portion of upper component 28. Supporting framework 20 comprises three upwardly open cradles 32, 33 and 34. Cradle 32 is sized and shaped to externally engage cylindrical barrel portion 15 of hypodermic syringe 14. Cradles 33 and 34 are sized and shaped to externally engage flange ears 17 of syringe barrel flange 16. Cradle 32 includes a pair of lower projecting pinch arms 36. A user can inwardly press arms 36 in the direction of each other to cause wider opening of the upper portion of cradle 32 for ease in inserting syringe barrel 15 therein. Cradles 33 and 34 are preferably sized to more loosely receive flange ears 17.

Cradle 32 comprises a pair of pivotal syringe support members 35 configured for pushing inwardly on a syringe held between them. Each pivotal syringe support member 35 comprises a syringe grasping cupped portion 39 and one of the pinch arm portions 36. Pivotal syringe support members 35 are connected to body 12 by longitudinal projecting stems 37. Pivotal syringe support members 35 are connected to one another by a transversely extending stem 38.

Body halves 28 and 30 internally receive a screw 40 for selective rotation relative to body 12. Screw 40 comprises opposing longitudinal ends 44 and 46 which are not threaded. Longitudinal end 44 is provided with a slot 45 configured for receiving a flat head screw driver. Slot 45 is accessible from longitudinal end 24 of body 12. Body halves 28 and 30 comprise two opposing pairs 41 and 42 of cooperating journal recesses which rotatably receive longitudinal ends 44 and 46 of screw 40. Recesses 41 rotatably receive longitudinal end 44 of screw 40, while recesses 42 rotatably receive longitudinal end 46 of screw 40.

Plunger stop 22 comprises a nut 50 which is threadedly engaged relative to screw 40. Nut 50 includes a lateral projection 52 sized and positioned to engage outermost head/end 19 of syringe plunger 18 received relative to supporting framework 20. Upper body portion 28, and thereby body 12, includes an elongated slot 55 within or through which lateral projection 52 extends and moves upon rotation of screw 40. For example, FIG. 1 illustrates an alternate adjusted plunger position 23 in phantom which can be achieved by proper rotation of screw 40.

In operation, for a visually impaired person for example, typically another person or care giver such a physician or nurse would adjust apparatus 10 such that plunger stop 22 is positioned at a desired location for desired precise quantity filling of a syringe 14 received by the apparatus. For example, FIG. 8 illustrates a vial 60 engaged relative to hypodermic syringe 14 received by apparatus 10. The person providing the injection would extend plunger 18 from hypodermic syringe 14 to the point where plunger head 19 firmly abuts lateral projection 52 of plunger stop 22. With plunger stop 22 having been pre-set relative to desired filling of a predetermined size or configured syringe 14, the desired dosage filling of the syringe is assured. Screw 40 is preferably provided in an example manner as shown to both enable easy subsequent adjustment by a care giver, but not so exposed to result in inadvertent adjustment by the patient which would adversely effect otherwise precise enabled positioning of plunger stop 22.

Figure 17:
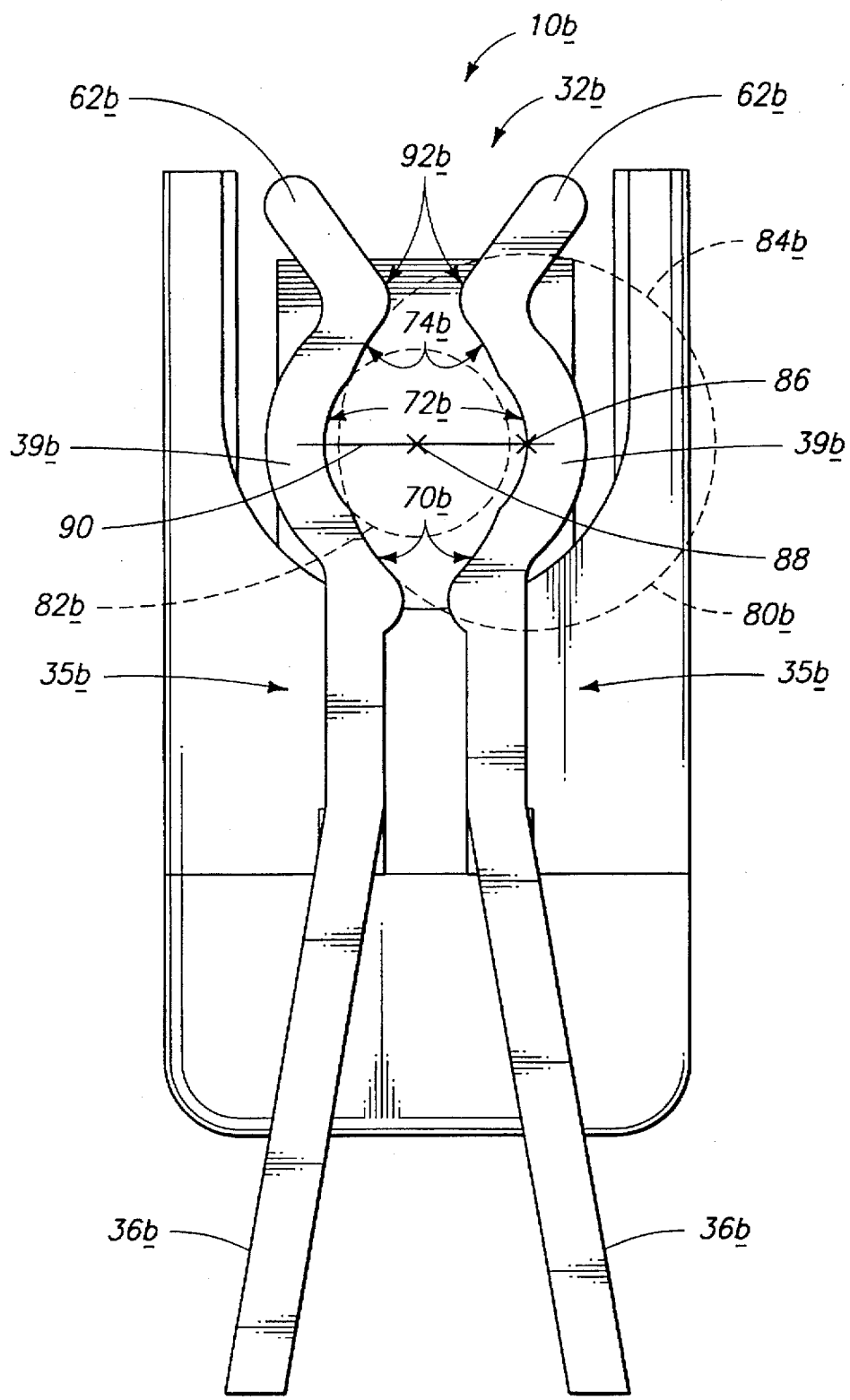
FIG. 17 is an enlarged front end view of the FIG. 9 syringe filling apparatus.
Figure 18:
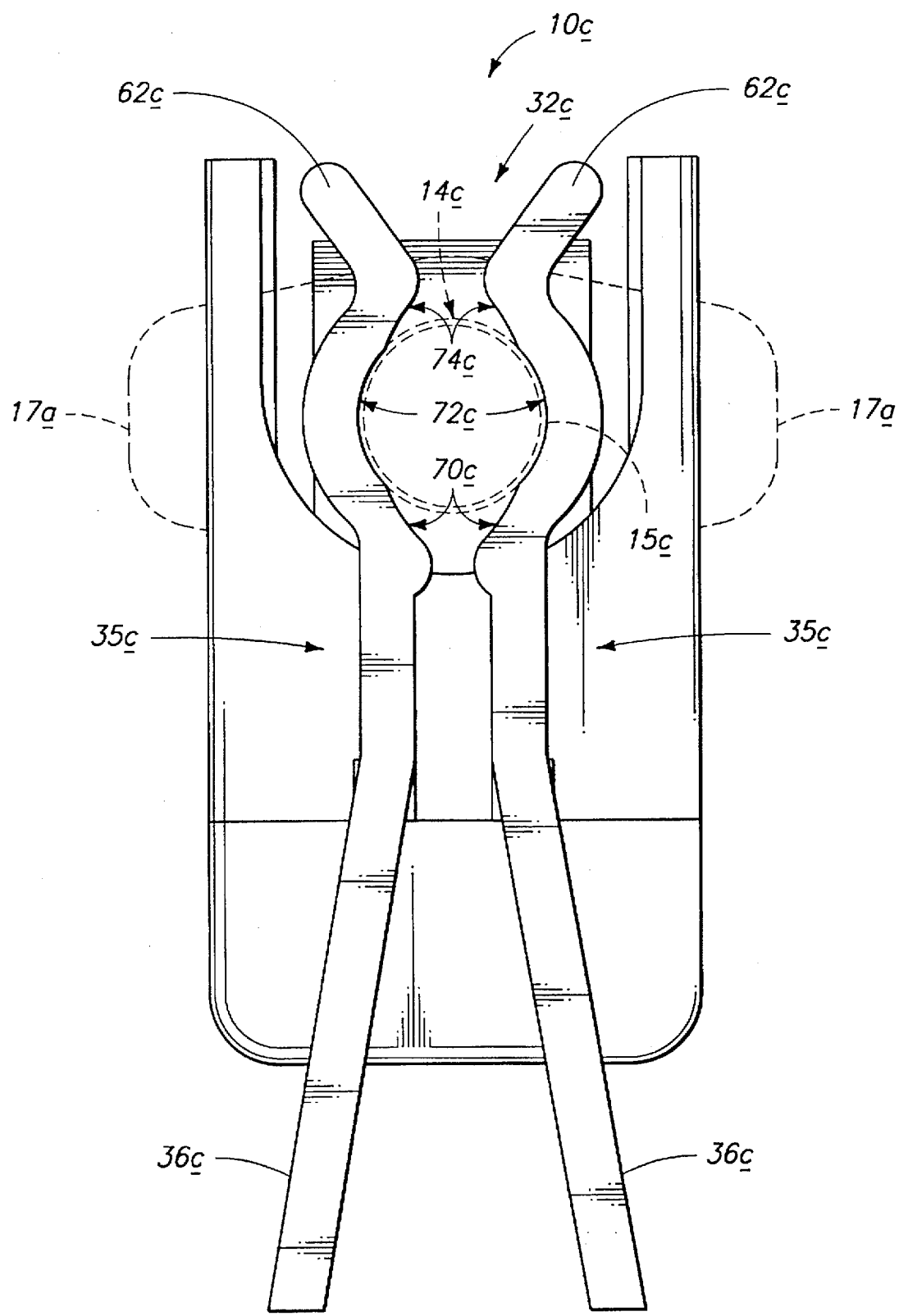
FIG. 18 is an enlarged front end sectional view of the FIG. 9 syringe filling apparatus shown with a small-diameter hypodermic syringe received by the apparatus.
Figure 19:
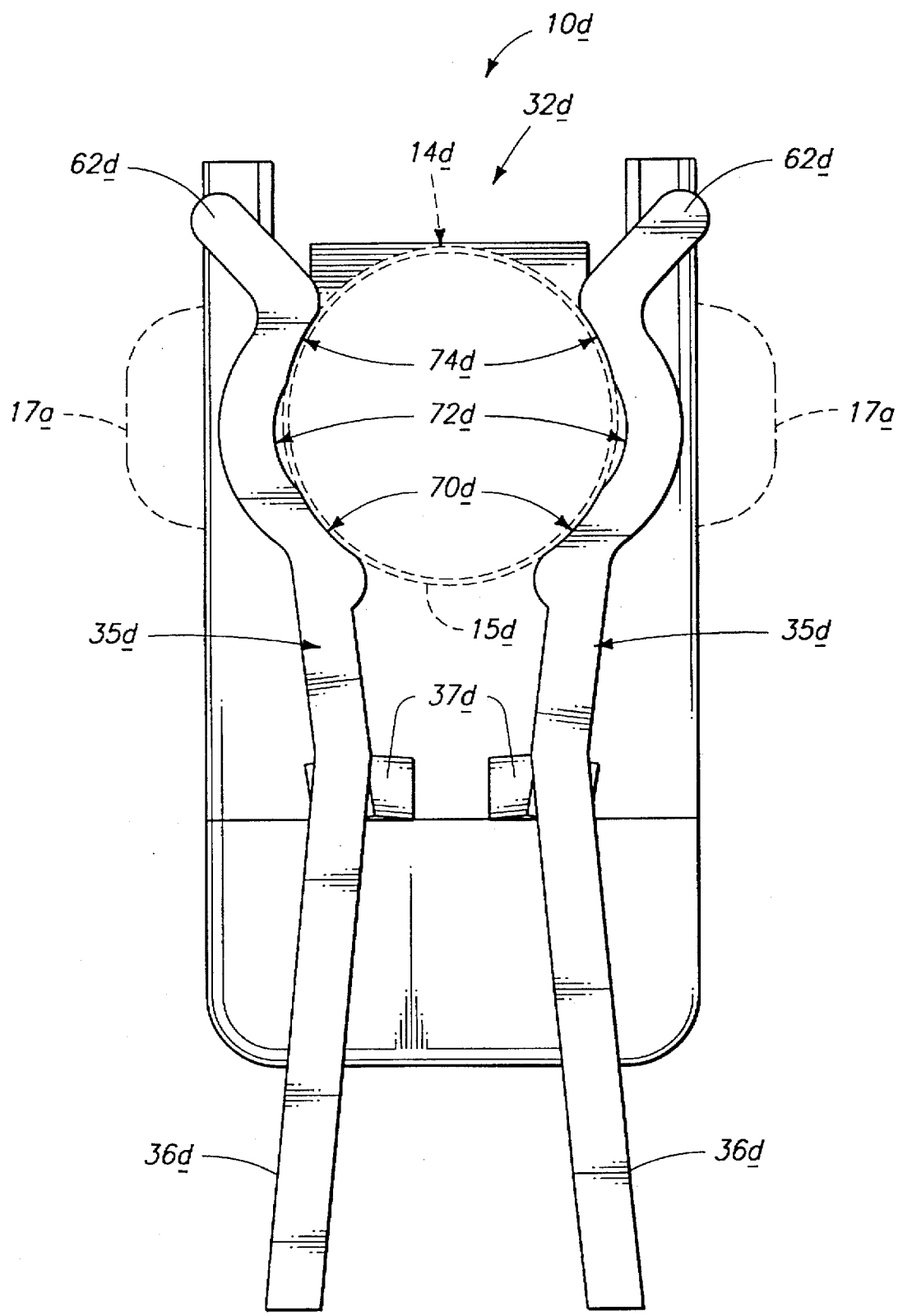
FIG. 19 is an enlarged front end sectional view of the FIG. 9 syringe filling apparatus shown with a large-diameter hypodermic syringe received by the apparatus.

Referring to FIGS. 9–19, a hypodermic syringe filling apparatus in accordance with a second embodiment of the invention is described. The second embodiment can preferably tightly grasp various sizes of syringes. The views of the second embodiment in FIGS. 9–16 are similar to the views of the first embodiment in FIGS. 1–8, respectively. The views of the second embodiment in FIGS. 17–19 are expanded front views of second embodiment illustrating how the second embodiment can tightly grasp syringes of differing sizes.

Referring first to FIGS. 9–16, like numerals from the preceding discussion of the first embodiment are utilized where appropriate, with differences being indicated by the suffix "a" or with different numerals. A hypodermic syringe filling apparatus of the second embodiment is indicated generally with reference numeral 10a. Such comprises a longitudinally elongated body 12a configured for retaining a hypodermic syringe 14a. For purposes of the continuing discussion, the illustrated example syringe 14a comprises a cylindrical barrel portion 15a, a syringe finger flange 16a having opposing flange ears 17a, a plunger 18a slidably received within barrel 15a, and a plunger head/end 19a.

A syringe supporting framework 20a is provided relative to body 12a and is sized to externally engage and retain hypodermic syringe 14a. A plunger stop 22a is associated with body 12a and positioned to engage and stop extension of plunger 18a of syringe 14a received by supporting framework 20a. Plunger stop 22a is mounted for movement relative to supporting framework 20a to a plurality of fixed locations to enable degree of extension of plunger 18a to be selectively varied.

More specifically, elongated body 12a has opposing longitudinal ends 24a and 26a. Syringe supporting framework 20a is provided at or adjacent longitudinal end 26a. Body 12a comprises a pair of juxtaposed pieces in the form of an upper portion 28a and a lower portion 30a which are adhered together, preferably by a weld. An example method of welding upper portion 28a and lower portion 30a together is a sonic welding process. Supporting framework 20a is formed at a fore portion of upper component 28a.

Supporting framework 20a comprises three upwardly open cradles 32a, 33a and 34a. Cradle 32a is sized and shaped to externally engage cylindrical barrel portion 15a of hypodermic syringe 14a. Cradles 33a and 34a are sized and shaped to externally engage flange ears 17a of syringe barrel flange 16a.

Cradle 32a includes a pair of pivotal syringe support members 35a configured for pushing inwardly on a syringe held between them. Pivotal syringe support members 35a comprise pinch arm portions 36a and syringe grasping cupped portions 39a adjacent pinch arm portions 36a. As shown in FIG. 13, syringe grasping cupped portions 39a comprise a first curved portion 70, a second curved portion 72, and a third curved portion 74. Curved portions 70, 72 and 74 can permit apparatus 10a to grasp syringes of widely varying sizes, as will be discussed in more detail below with reference to FIGS. 17–19.

Pinch arm portions 36a are configured for inward movement toward one another. A user can inwardly press pinch arm portions 36a in the direction of each other to cause a wider opening of the upper portion of cradle 32a for ease in inserting syringe barrel 15a therein.

Pivotal syringe support members 35a further comprise syringe slide portions 62 adjacent syringe grasping cupped portions 39a. In the shown preferred embodiment, syringe slide portion 62 extend upwardly and outwardly from third radial portion 74, and comprise a substantially planar upper surface 63. Syringe slide portions 62 can direct barrel 15a of syringe 14a into cradle 32a and thereby simplify insertion of barrel 15a into cradle 32a.

Pivotal syringe support members 35a are connected to body 12a by a pair of longitudinally projecting stems 37a. In contrast to the above-discussed first embodiment, the second embodiment lacks a transverse stem between pivotal syringe support members 35a (such as transverse stem 38 shown in FIG. 5). This difference between the first and second embodiment can be seen by comparing FIG. 5, illustrating a front view of the first embodiment, with FIG. 13 illustrating a front view of the second embodiment.

Because the second embodiment lacks a transverse stem between pivotal members 35a, longitudinally projecting stems 37a move inwardly toward one another as pinch arm portions 36a are pressed inwardly.

Pivotal syringe support members 35a comprise links "X" and widths "Y". As there is no transverse stem between support members 35a, syringe filling apparatus 10a comprises a space 64 between pivotal syringe support members 35a which spans lengths "X" and widths "Y".

Body halves 28a and 30a internally receive a screw 40a for selective rotation relative to body 12a. Screw 40a comprises opposing longitudinal ends 44a and 46a which are not threaded. Longitudinal end 44a is provided with a slot 45a configured for receiving a flat head screw driver. Slot 45a is accessible from longitudinal end 24a of body 12a. Body halves 28a and 30a comprise two opposing pairs 41a and 42a of cooperating journal recesses which rotatably receive longitudinal ends 44a and 46a of screw 40a. Recesses 41a rotatably receive longitudinal end 44a of screw 40a, while recesses 42a rotatably receive longitudinal end 46a of screw 40a.

Plunger stop 22a comprises a nut 50a which is threadedly engaged relative to screw 40a. Nut 50a includes a lateral projection 52a sized and positioned to engage outermost head/end 19a of syringe plunger 18a received relative to supporting framework 20a. In contrast to lateral projection 52 (shown, for example, in FIG. 2) lateral projection 52a has a more wedge-shaped side construction as evidenced by comparing FIG. 10 with FIG. 2. Upper body portion 28a, and thereby body 12a, includes an elongated slot 55a within or through which lateral projection 52a extends and moves upon rotation of screw 40a. For example, FIG. 9 illustrates an alternate adjusted plunger position 23a in phantom which can be achieved by proper rotation of screw 40a.

In operation, for a visually impaired person for example, typically another person or care giver such a physician or nurse would adjust apparatus 10a such that plunger stop 22a is positioned at a desired location for desired precise quantity filling of a syringe 14a received by the apparatus. For example, FIG. 16 illustrates a vial 60a engaged relative to hypodermic syringe 14a received by apparatus 10a. The person providing the injection would extend plunger 18a from hypodermic syringe 14a to the point where plunger head 19a firmly abuts lateral projection 52a of plunger stop 22a. With plunger stop 22a having been pre-set relative to desired filling of a predetermined size or configured syringe 14a, the desired dosage filling of the syringe is assured. Screw 40a is preferably provided in an example manner as shown to both enable easy subsequent adjustment by a care giver, but not so exposed to result in inadvertent adjustment by the patient which would adversely effect otherwise precise enabled positioning of plunger stop 22a.

Referring next to FIGS. 17–19, a hypodermic syringe filling apparatus of the second embodiment is illustrated in enlarged front end view without a syringe (FIG. 17), grasping a small syringe (FIG. 18), and grasping a large syringe (FIG. 19). In referring to FIGS. 17, 18 and 19, like numerals from the preceding discussion of FIGS. 9–16 will be utilized, with the difference that the suffix "a" will be replaced by the suffixes "b", "c", and "d", respectively.

Referring to FIG. 17, syringe filling apparatus 10b comprises a pair of pivotal syringe support members 35b. Pivotal syringe support members 35b comprise syringe grasping cupped portions 39b, which in turn comprise a first curved portion 70b, a second curved portion 72b, and a third curved portion 74b. First, second and third curved portions 70b, 72b and 74b comprise first, second and third curvatures, respectively. Preferably, second curved portion 72b comprises a greater curvature than first and third curved portions 70b and 74b. Most preferably, curved portions 70b, 72b and 74b are radial portions of first, second and third circles, respectively, with the second circle comprising a smaller radius than the first and third circles. More preferably, the first and third circles will comprise substantially equal radii, and even more preferably, the first and third circles will overlay one another.

A most preferred orientation of circles corresponding to radial portions 70b, 72b and 74b of the leftmost syringe support member 35b is illustrated in FIG. 17. Circle 80b corresponds to radial portion 70b, circle 82b corresponds to radial portion 72b, and circle 84b corresponds to radial portion 74b. As shown, circles 80b and 84b overlay one another and are larger than circle 82b. Overlaid circles 80b and 84b share a center 86, and circle 82b has a center 88. Centers 86 and 88 lie along a plane 90 which approximately bisects second radial portion 72b.

A preferred radius of circle 82b is about 0.1 inches, and a preferred radius of circles 80b and 84b is about 0.2015 inches. Such preferred measurements can enable apparatus 10b to grasp syringes having diameters of from about 3/16 inches (0.1875 inches) to about 3/8 inches (0.375 inches). Shown in FIG. 18, discussed below, is an apparatus 10c having the preferred measurements and grasping a syringe barrel 15c having a diameter of about 3/16 inches, and shown in FIG. 19, discussed below, is an apparatus 10d having the preferred measurements and grasping a syringe barrel 15d having a diameter of about 3/8 inches.

Syringe slide portions 62b are adjacent third curved portions 74b and extend upwardly and outwardly therefrom. Syringe slide portions 62b connect with curved portions 74b via corners 92b. Preferably, corners 92b are radial portions comprising a segment of a circle. An example preferred construction utilizes corners 92b which are segments of a circle having a radius of about 0.04 inches.

Referring to FIG. 18, a syringe filling apparatus 10c is illustrated grasping a relatively small syringe 14c within cradle 32c. Syringe 14c comprises a barrel portion 15c which is grasped substantially entirely within the smaller second radial portion 72c.

Referring to FIG. 19, a syringe filling apparatus 10d is illustrated grasping a relatively large syringe 14d within cradle 32d. Syringe 14d comprises a barrel portion 15d which is grasped substantially entirely by the larger radial portions 70d and 74d. In comparing FIGS. 18 and 19, it is noted that the multiple radial portions 70, 72 and 74 of the second embodiment syringe holding apparatus of the present invention enable the apparatus to tightly grasp syringe barrels 15c and 15d having widely different diameters. Accordingly, the second embodiment syringe filling apparatus of FIGS. 9–19 can be utilized in diverse applications requiring diverse syringe barrel sizes.

FIG. 19 illustrates a further aspect of the preferred embodiment of a syringe holding apparatus 10d of the present invention. Specifically, syringe holding apparatus 10d preferably comprises longitudinally extending stems 37d which can substantially twist along their longitudinal axes. Such substantial twisting of longitudinal stems 37d enables wide opening of cradle 32d for accommodation of wide syringe barrels.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

I claim:

1. A hypodermic syringe filling apparatus enabling filling of a hypodermic syringe with a prescribed quantity of fluid, the filling apparatus comprising:

a pair of pivotal syringe support members configured for pushing inwardly on a syringe held between them; the respective pivotal syringe support members comprising:

pinch arm portions;

syringe grasping cupped portions adjacent the pinch arm portions, the syringe grasping cupped portions comprising first, second and third radial portions; the second radial portion being positionally between the first and the third radial portions; the first, second and third radial portions comprising segments of first, second, and third circles, respectively, the second circle comprising a smaller radius than the first and third circles;

syringe slide portions adjacent the syringe grasping cupped portions; and the pair of pivotal syringe support members together comprising an upwardly open cradle sized and shaped to externally engage a cylindrical syringe barrel portion of a hypodermic syringe.

2. The hypodermic syringe filling apparatus of claim 1 wherein the pinch arm portions are configured for inward movement toward one another, the pivotal syringe support members being configured to couple inward movement of the pinch arms to widening of an opening of the upwardly open cradle.

3. The hypodermic syringe filling apparatus of claim 1 wherein the first and third circles comprise substantially equal radii.

4. The hypodermic syringe filling apparatus of claim 1 wherein the first and third circles overlay one another.

5. The hypodermic syringe filling apparatus of claim 1 wherein the first and third circles overlay one another and share a first center; wherein the second circle has a second center; and wherein the first and second centers lie along a plane which approximately bisects the second radial portions of the pivotal syringe support members.

6. The hypodermic syringe filling apparatus of claim 1 further comprising a longitudinally elongated body; wherein the pair of pivotal syringe support members are connected to the body by a pair of longitudinally projecting stems, and wherein the longitudinally projecting stems move inwardly toward one another as the pinch arm portions are pressed inwardly.

7. The hypodermic syringe filling apparatus of claim 1 wherein the pair of pivotal syringe support members comprise lengths and widths; the syringe filling apparatus further comprising a space between the pivotal syringe support members spanning the lengths and widths of the pivotal syringe support members.

8. A hypodermic syringe filling apparatus enabling filling of a hypodermic syringe with a prescribed quantity of fluid, the filling apparatus comprising:

a pair of pivotal syringe support members configured for pushing inwardly on a syringe held between them; the respective pivotal syringe support members comprising:

pinch arm portions;

syringe grasping cupped portions adjacent the pinch arm portions; and wherein the pair of pivotal syringe support members comprise lengths and widths; the syringe filling apparatus further comprising a space between the pivotal syringe support members spanning the lengths and widths of the pivotal syringe support members.

9. A hypodermic syringe filling apparatus enabling filling of a hypodermic syringe with a prescribed quantity of fluid, the filling apparatus comprising:

a longitudinally elongated body having opposing longitudinal ends;

a pair of pivotal syringe support members provided relative to the body adjacent one of the longitudinal ends; the pivotal syringe support members being configured for pushing inwardly on a syringe held between them; the respective pivotal syringe support members comprising:

pinch arm portions;

syringe grasping cupped portions adjacent the pinch arm portions, the syringe grasping cupped portions comprising first, second and third radial portions; the second radial portion being positionally between the first and the third radial portions; the first, second and third radial portions comprising segments of first, second, and third circles, respectively, the second circle comprising a smaller radius than the first and third circles;

syringe slide portions adjacent the syringe grasping cupped portions;

the pair of pivotal syringe support members together comprising a first upwardly open cradle, the first upwardly open cradle being sized and shaped to externally engage a cylindrical syringe barrel portion of a hypodermic syringe; and the pinch arm portions being configured for inward movement toward one another, the pivotal syringe support members being configured to couple inward movement of the pinch arms to widening of an opening of the first upwardly open cradle;

a second upwardly open cradle longitudinally displaced from the first upwardly open cradle, the second upwardly open cradle being sized and shaped to externally engage a syringe barrel flange of the hypodermic syringe received by the first upwardly open cradle; and a plunger stop associated with the body and positioned to engage and stop extension of a plunger of a hypodermic syringe received by the first and second upwardly open cradles, the plunger stop being mounted for movement relative to the first and second upwardly open cradles to a plurality of fixed locations to enable degree of extension of a plunger of a hypodermic syringe received by the first and second upwardly open cradles to be selectively varied.

10. The hypodermic syringe filling apparatus of claim 9 wherein the first and third circles comprise substantially equal radii.

11. The hypodermic syringe filling apparatus of claim 9 wherein the first and third circles overlay one another.

12. The hypodermic syringe filling apparatus of claim 9 wherein the first and third circles overlay one another and share a first center; wherein the second circle has a second center; and wherein the first and second centers lie along a plane which approximately bisects the second radial portions of the pivotal syringe support members.

13. The hypodermic syringe filling apparatus of claim 9 wherein the pair of pivotal syringe support members are connected to the body by a pair of longitudinally projecting stems, and wherein the longitudinally projecting stems move inwardly toward one another as the pinch arm portions are pressed inwardly.

14. The hypodermic syringe filling apparatus of claim 9 wherein the pair of pivotal syringe support members comprise lengths and widths; the syringe filling apparatus further comprising a space between the pivotal syringe support members spanning the lengths and widths of the pivotal syringe support members.

15. The hypodermic syringe filling apparatus of claim 9 further comprising a screw mounted for selective rotation relative to the body, the plunger stop threadedly engaging the screw, the screw having opposing longitudinal ends, the body comprising a pair of juxtaposed portions mounted to one another, the juxtaposed portions comprising two opposing pairs of journal recesses which rotatably receive the respective opposing longitudinal ends of the screw.

16. The hypodermic syringe grasping apparatus of claim 9 further comprising a syringe slide adjacent the third radial portion; the syringe slide extending upwardly and outwardly from the third radial portion.

17. The hypodermic syringe grasping apparatus of claim 9 further comprising a syringe slide adjacent the third radial portion; the syringe slide extending upwardly and outwardly from the third radial portion and comprising a substantially planar upper surface.

18. A hypodermic syringe filling apparatus enabling filling of a hypodermic syringe with a prescribed quantity of fluid, the filling apparatus comprising:

a longitudinally elongated body having opposing longitudinal ends;

a syringe supporting framework provided adjacent to one of the longitudinal ends of the body, the framework being sized to externally engage and retain a hypodermic syringe, the supporting framework comprising at least three upwardly open cradles, a first of the cradles being sized and shaped to externally engage a cylindrical barrel portion of a hypodermic syringe received by the supporting framework, a second and a third of the cradles being sized and shaped to externally engage a syringe barrel flange of a hypodermic syringe received by the supporting framework, the supporting framework further comprising a pair of lower projecting pinch arms attached to the first cradle, the pinch arms being configured for inward movement toward one another, the pinch arms and the first cradle being together configured to couple inward movement of the pinch arms to widening of the upward opening of the first cradle; the first cradle opening comprising a first, second and third radial portion, the second radial portion being between the first and third radial portions, the first, second and third radial portions comprising segments of first, second, and third circles, respectively, the second circle comprising a smaller radius than the first and third circles;

a plunger stop associated with the body and positioned to engage and stop extension of a plunger of a hypodermic syringe received by the supporting framework, the plunger stop being mounted for movement relative to the supporting framework to a plurality of fixed locations to enable degree of extension of a plunger of a hypodermic syringe received by the supporting framework to be selectively varied; and a screw mounted for selective rotation relative to the body, the plunger stop threadedly engaging the screw, the screw having opposing longitudinal ends, the body comprising a pair of juxtaposed portions mounted to one another, the juxtaposed portions comprising two opposing pairs of journal recesses which rotatably receive the respective opposing longitudinal ends of the screw, the plunger stop comprising a nut, the nut threadedly engaging the screw, the nut comprising a lateral projection sized and positioned to engage an outermost head end of a plunger of a hypodermic syringe received by the supporting framework, the body including an elongated open slot within which the lateral projection moves upon rotation of the screw.

19. The hypodermic syringe filling apparatus of claim 18 wherein the first and third circles comprise substantially equal radii.

20. The hypodermic syringe filling apparatus of claim 18 wherein the first and third circles overlay one another.

21. The hypodermic syringe filling apparatus of claim 18 wherein the pair of independently pivotal syringe support members are connected to the body by a pair of longitudinally projecting stems, and wherein the longitudinally projecting stems move inwardly toward one another as the pinch arm portions are pressed inwardly.

22. The hypodermic syringe filling apparatus of claim 18 wherein the pair of independently pivotal syringe support members comprise lengths and widths; the syringe filling apparatus further comprising a space between the pivotal syringe support members spanning the lengths and widths of the pivotal syringe support members.

23. A hypodermic syringe grasping apparatus comprising:
a pair of syringe support members configured for pushing inwardly on a syringe held between them; at least one of the pivotal syringe support members comprising:
a syringe grasping portion comprising a first curved portion and a second curved portion; the first and second curved portions comprising a first curvature and a second curvature, respectively; and
the pair of pivotal syringe support members together comprising an upwardly open cradle sized and shaped to externally engage a cylindrical syringe barrel portion of a hypodermic syringe.

24. The hypodermic syringe grasping apparatus of claim 23 wherein both syringe support members comprise said syringe grasping portion.

25. The hypodermic syringe grasping apparatus of claim 23 wherein the first and second curvatures are different from one another.

26. The hypodermic syringe grasping apparatus of claim 23 wherein the syringe grasping portion further comprises a third curved portion.

27. The hypodermic syringe grasping apparatus of claim 23 wherein the syringe grasping portion further comprises a third curved portion; the third curved portion having a third curvature; the third curvature be substantially equal to the first curvature and being less than the second curvature.

28. The hypodermic syringe grasping apparatus of claim 23 further comprising a third curved portion; the third curved portion having a third curvature; the third curvature be substantially equal to the first curvature and being less than the second curvature; the second curve being positionally between the first and third curved portions.

29. The hypodermic syringe grasping apparatus of claim 23 further comprising a syringe slide adjacent one of the curved portions; the syringe slide extending upwardly and outwardly from the curved portion.

30. The hypodermic syringe grasping apparatus of claim 23 further comprising a syringe slide adjacent one of the curved portions; the syringe slide extending upwardly and outwardly from the curved portion and comprising a substantially planar upper surface.

31. A hypodermic syringe grasping apparatus comprising an individual pivotal syringe support member having a first curved portion and a second curved portion adjacent the first curved portion, the first and second curved portions comprising a first curvature and a second curvature, respectively; and the first and second curvatures being different from one another.

32. A hypodermic syringe grasping apparatus comprising:
an individual pivotal syringe support member having a first curved portion, a second curved portion adjacent the first curved portion, and a third curved portion adjacent the second curved portion; the first, second and third curved portions comprising a first curvature, a second curvature and a third curvature, respectively; and at least one of the first, second and third curvatures being different from another of the first, second and third curvatures.

33. A hypodermic syringe grasping apparatus comprising:
a longitudinally elongated body having opposing longitudinal ends;
a syringe supporting framework provided adjacent to one of the longitudinal ends of the body, the framework being sized to externally engage and retain a hypodermic syringe, the supporting framework comprising:
at least three upwardly open cradles, a first of the cradles being sized and shaped to externally engage a cylindrical barrel portion of a hypodermic syringe received by the supporting framework, a second and a third of the cradles being sized and shaped to externally engage a syringe barrel flange of a hypodermic syringe received by the supporting framework; the first cradle comprising an opening; the first cradle opening comprising a first, second and third radial portion, the second radial portion being between the first and third radial portions, the first, second and third radial portions comprising segments of first, second, and third circles, respectively, the second circle comprising a smaller radius than the first and third circles;
a pair of lower projecting pinch arms attached to the first cradle, the pinch arms being configured for inward movement toward one another, the pinch arms and the first cradle being together configured to couple inward movement of the pinch arms to widening of the opening of the first cradle.

34. The hypodermic syringe grasping apparatus of claim 33 wherein the first and third circles comprise substantially equal radii.

35. The hypodermic syringe grasping apparatus of claim 33 further comprising a syringe slide adjacent the third radial portion; the syringe slide extending upwardly and outwardly from the third radial portion.

36. The hypodermic syringe grasping apparatus of claim 33 further comprising a syringe slide adjacent the third radial portion; the syringe slide extending upwardly and outwardly from the third radial portion and comprising a substantially planar upper surface.

* * * * *